(12) United States Patent
Duchateau et al.

(10) Patent No.: US 12,202,853 B2
(45) Date of Patent: *Jan. 21, 2025

(54) EPOXIDE POLYENE AMPHOTERIC MACROLIDE AND PROCESS FOR PURIFYING NATAMYCIN

(71) Applicant: DSM IP ASSETS B.V., Heerlen (NL)

(72) Inventors: Alexander Lucia Leonardus Duchateau, Echt (NL); Peter Philip Lankhorst, Echt (NL); Willebrordus Bernardus Van Scheppingen, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 50 days.

This patent is subject to a terminal disclaimer.

(21) Appl. No.: 18/156,750

(22) Filed: Jan. 19, 2023

(65) Prior Publication Data

US 2023/0151045 A1 May 18, 2023

Related U.S. Application Data

(63) Continuation of application No. 17/268,252, filed as application No. PCT/EP2019/071900 on Aug. 15, 2019, now Pat. No. 11,591,360.

(30) Foreign Application Priority Data

Aug. 16, 2018 (EP) .................................. 18189250

(51) Int. Cl.
C07H 17/08 (2006.01)
(52) U.S. Cl.
CPC .................... C07H 17/08 (2013.01)

(58) Field of Classification Search
None
See application file for complete search history.

(56) References Cited

U.S. PATENT DOCUMENTS

| | | | |
|---|---|---|---|
| 2,631,143 | A | 3/1953 | Braker et al. |
| 7,727,966 | B2 | 6/2010 | De Haan et al. |
| 7,816,332 | B2 | 10/2010 | Stark et al. |
| 8,420,609 | B2 | 4/2013 | De Haan et al. |
| 9,096,633 | B2 | 8/2015 | De Haan et al. |
| 9,615,581 | B2 | 4/2017 | De Haan et al. |

FOREIGN PATENT DOCUMENTS

| | | |
|---|---|---|
| CN | 105342987 A | 2/2016 |
| WO | 9507998 A1 | 3/1995 |
| WO | 9729207 A1 | 8/1997 |
| WO | 2004105491 A1 | 12/2004 |
| WO | 2006045831 A1 | 5/2006 |

OTHER PUBLICATIONS

International Search Report received in international application No. PCT/EP2019/071900, mailed Oct. 10, 2019.
Brik et al., "Natamycin," Analytical Profiles of Drug Substa., Jan. 1, 1981, pp. 538-540.

*Primary Examiner* — Layla D Berry
(74) *Attorney, Agent, or Firm* — McBee, Moore & Vanik IP, LLC

(57) ABSTRACT

The present invention is directed to a process for purifying natamycin, to an epoxide polyene amphoteric macrolide, to a composition comprising said polyene amphoteric macrolide and to a process for preparing said polyene amphoteric macrolide.

10 Claims, No Drawings

EPOXIDE POLYENE AMPHOTERIC MACROLIDE AND PROCESS FOR PURIFYING NATAMYCIN

CROSS-REFERENCE TO RELATED APPLICATIONS

This application is a continuation U.S. application Ser. No. 17/268,252, filed 12 Feb. 2021, which is a National Stage entry of International Application No. PCT/EP2019/071900, filed 15 Aug. 2019, which claims priority to European Patent Application No. 18189250.6, filed 16 Aug. 2018, the contents of each of which are hereby incorporated by reference.

BACKGROUND

Field

The present invention is directed to a process for purifying natamycin, to an epoxide polyene amphoteric macrolide, to a composition comprising said polyene amphoteric macrolide and to a process for preparing said polyene amphoteric macrolide.

Description of Related Art

Natamycin (structural formula (I), pimaricin, $C_{33}H_{47}NO_{13}$, CAS number 7681-93-8, (1R,3S,5R,7R, 8E, 12R, 14E, 16E, 18E,20E,22R,24S,25R,26S)-22-[(3-amino-3,6-dideoxy-β-D-mannopyranosyl)oxy]-1,3,26-trihydroxy-12-methyl-10-oxo-6, 11,28

(I)

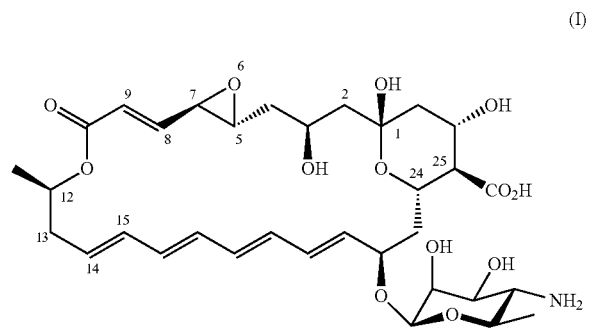

trioxatricyclo[22.3.1.0$^{5,7}$]octacosa-8, 14, 16, 18, 20-pentaene-25-carboxyl ic acid) is an all-trans epoxide polyene amphoteric macrolide antifungal used to treat fungal infections around the eye. This includes infections of the eyelids, conjunctiva, and cornea. Natamycin is also used in the food industry as a preservative for dairy products like cheese, and also as a preservative for meat products like sausages and for fruit.

Access to naturally produced molecules in high purity is of key importance for multiple reasons such as optimization of atom efficiency, minimalization of waste and avoiding unwanted side effects by contaminants. Especially for pharmaceutical applications the bar on purity is high and natamycin is no exception to this rule.

Natamycin is produced by fermentation of the bacterium *Streptomyces natalensis* after which the product usually is obtained in the form of plate-like crystals. One of the problems associated with natamycin is related to its low solubility in aqueous environment and the resulting fact that aqueous formulations are in the form of suspensions. In its original form, natamycin crystals sediment rapidly, which makes natamycin suspensions not user friendly and difficult to dispense evenly. WO 2006/045831 describes recrystallization in aqueous environment by dissolving at either low or high pH followed by re-setting of the pH to neutral to yield small, needle-shaped crystals. The latter re-crystallization process is well suited for application on industrial scale and solves the problem of unwanted rapid sedimentation of natamycin suspensions by virtue of the crystal morphology.

Further, or alternative, improvements with respect to purity can in theory be achieved by chromatographic techniques. Unfortunately, as stated above the main problem in (preparative) chromatographic purification is the low solubility of natamycin in aqueous environment. Consequently, sufficiently high concentrations cannot be reached and as a result designing an efficient process towards further purified natamycin is not possible. Although chromatographic methods have been reported in scientific literature, all are designed to detect and quantify natamycin in various samples and are not of a preparative nature. Consequently, these methods never disclose larger concentrations of natamycin to be applied on chromatographic material nor is there any suggestion indicating how this would be achievable. In practice, the above documentation discloses natamycin concentrations ranging from 0.02 to 1 mg/L, which even is significantly below the solubility of natamycin in water at neutral pH (around 40 mg/L). It is possible to achieve higher concentrations of dissolved natamycin however this requires the addition of substantial amounts of organic solvents as described e.g. in WO 2004/105491, WO 95/07998 and in H. Brik in '*Analytical Profiles of Drug Substances*' (1981) 10, 513-561.

The same problem also prevents the isolation, preparation, identification, and analysis of compounds that are present in natamycin samples in extremely low amounts and which were hitherto not detected or, depending on source or production process of natamycin, perhaps not even present. Having access to such compounds would be a desirable tool in further analyzing, helping understand and optimizing not only the product natamycin but where applicable also its production process.

The present invention seeks to overcome the above problems, by providing a liquid solution of natamycin in combination with a metal salt of a carboxylic acid for use in a chromatographic purification process. Furthermore, the present invention is directed at isolating and identifying hitherto unknown trace compounds that may be present in natamycin.

SUMMARY

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article.

In the context of the invention the term "solution" refers to a composition in which one component (or mixture of components) is dissolved in another component (or mixture of components). When the one component (or mixture of components) is not (fully), i.e. partially, dissolved in another component (or mixture of components), the composition is referred to as a "suspension". For example, a composition comprising 999.98 g of water and 0.02 g of natamycin (i.e. 20 ppm) wherein the natamycin is fully dissolved is referred to as a (20 ppm) solution of natamycin in water, whereas a composition comprising 999.8 g of water and 0.2 g of natamycin (i.e. 200 ppm) wherein the natamycin is partially dissolved is referred to as a (200 ppm) suspension of natamycin in water. In the context of the invention, a solution is defined as a liquid mixture which, after centrifugation for at least 10 min at 3000 rpm, results in a pellet and a supernatant, the pellet after removal of supernatant and drying representing no more than 0.001% of the weight of the starting solution before centrifugation.

In a first aspect, the invention provides a process for purifying natamycin comprising mixing a composition comprising crude natamycin, a metal salt of a carboxylic acid and water and subjecting the resulting mixture to chromatography whereby fractions are collected and selected fractions that comprise natamycin are combined, wherein the amount of said crude natamycin is from 1 g to 100 g/kg of the total weight of said composition and wherein the concentration of said metal salt of a carboxylic acid is from 0.1 mol/L to 5 mol/L.

DETAILED DESCRIPTION OF A PREFERRED EMBODIMENT

In the context of the present invention, purification of natamycin by chromatography is not straightforward. Although various chromatographic procedures may be envisaged, or are known, these are developed for analytical purposes and involve the application of samples at very low concentration. The latter is important to accommodate for the low solubility of natamycin in aqueous systems at neutral pH. For chromatographic purification of natamycin on preparative scale these methods are not suitable as the maximal amounts of natamycin are too low to isolate quantitative amounts. There are no methods known to dissolve natamycin in high concentration at suitable pH values in aqueous systems, i.e. systems that do not comprise components, like e.g. organic solvents, strong acids or bases, that negatively influence the chromatographic separation or even the chromatographic material as such. The combination of natamycin with a metal salt of a carboxylic acid at high concentrations as such is known, albeit for different purposes and/or not in the form of an aqueous solution. For example, CN 105342987 discloses a gel comprising various components, including natamycin and potassium sorbate, for the treatment of oral ulcers. Use of the same combination, or other metal salts of carboxylic acids, for controlling the growth of fungi is also described in EP 2749166, U.S. Pat. No. 5,738,888, WO 2009/010547, and P. Onsberg et al. (Sabouradia (1978) 16, 39-46), the latter combined with as much as 60% dimethyl sulfoxide.

By applying relatively high concentrations of metal salt of a carboxylic acid, like from 0.1 mol/L to 10 mol/L or from 0.5 mol/L to 5 mol/L or from 1 mol/L to 2.5 mol/L, natamycin is dissolved at high concentrations like from 1 g/L to 100 g/L, or from 2 g/L to 75 g/L or from 5 g/L to 60 g/L. The pH value of the solution of the invention is, measured at 20±2° C., from 6.0 to 11, often from 6.5 to 10, or from 7.0 to 9.5. At such pH values the solubility of natamycin in water normally is much lower, for example, at neutral pH values this is around 0.04 g/L (40 ppm).

In an embodiment, the metal which is part of the metal salt of a carboxylic acid is an alkali metal or an alkali earth metal, examples of which are calcium, lithium, magnesium, potassium, or sodium. Practically, good results are obtained when the metal is potassium or sodium.

In another embodiment, the carboxylic acid comprises from 1 to 7 carbon atoms. Examples are acetic acid, benzoic acid, citric acid, formic acid, lactic acid, propionic acid, sorbic acid but also mixtures thereof. Good examples are carboxylic acids with 3 carbon atoms such as lactic acid and propionic acid and carboxylic acids with 6 carbon atoms such as citric acid and sorbic acid. The carboxylic acid may be unsaturated with one or more double bonds. The double bounds may be cis or trans oriented. A good example is a carboxylic acid having two trans oriented double bonds such as sorbic acid. The carboxylic acid may contain hydroxyl groups, such as citric acid and lactic acid. The carboxylic acid may have a single carboxyl function, but also two, three or more.

In an embodiment, the above mixing is carried out at a temperature which is elevated for a certain period. It is found that not only dissolution of natamycin occurs faster, but also high final concentrations of natamycin are obtained and often the resulting solutions display improved stability. Thus, a temporary increase of temperature to from 30° C. to 130° C., or from 60° C. to 120° C., or from 70° C. to 110° C. may be applied for from 2 to 200 minutes, or from 3 to 100 minutes, or from 4 to 60 minutes.

Remarkably, the stability of natamycin in the solution obtained above is high and the concentration of natamycin remains at high values, also after prolonged periods of time. This effect is the most pronounced where the carboxylic acid is sorbic acid. Also, this effect is most pronounced when the metal is and alkali metal such as potassium. Accordingly, the solution of the invention unexpectedly does not require further auxiliary materials such as chelating agents like EDTA or antioxidants to warrant chemical stability described in the prior art.

Accordingly, the mixing of natamycin with a metal salt of a carboxylic acid results in solutions of high concentration that can be advantageously applied in preparative chromatography, an approach that has not been demonstrated or suggested in the art.

In another embodiment, a diol may be added to the composition comprising natamycin, a metal salt of a carboxylic acid and water. The diol may be added before, during, or after the other components are mixed. The diol preferably has a boiling point of between 125° C. and 300° C. or between 150° C. and 250° C. and the amount of diol is from 50 g/kg to 950 g/kg of the total weight of the composition. It is observed that addition of a diol to the solution of the invention resulted in further enhancement of the stability and or a further increase of solubility of natamycin. Suitable diols are dipropylene glycol, ethylene glycol, polyethylene glycol, propylene glycol or mixtures thereof.

The ratio of metal salt of a carboxylic acid to natamycin is from 0.1 (w/w) to 50 (w/w), or from 0.2 (w/w) to 45 (w/w), or from 0.5 (w/w) to 25 (w/w), or from 1 (w/w) to 10 (w/w). Alternatively, on a molar basis, the ratio of metal salt of a carboxylic acid to natamycin is from 0.5 (mole/mole) to 250 (mole/mole), or from 1 (mole/mole) to 100 (mole/mole), or from 2.5 (mole/mole) to 50 (mole/mole), or from 5 (mole/mole) to 45 (mole/mole).

An embodiment of the invention is the use of highly concentrated natamycin solutions that are subjected to chromatography. Thus, the chromatographic processes of the invention are advantageously carried out at unprecedented large scale. For example, when the chromatographic processes of the invention are carried out batch-wise, the amount of natamycin applied to the chromatographic material may be from 1 g to 10 kg per batch, or from 5 g to 5 kg per batch, or from 25 g to 1 kg per batch. In an example it was found that high input concentrations can be achieved by dissolving the natamycin feed in high molar potassium sorbate.

The term "preparative chromatography" relates to methods of separating mixtures of compounds which are dissolved in the mobile phase, of sufficient scale to isolate relevant quantities of the compound desired. Such methods are known in the art. A suitable method for preparative chromatography is, for instance, adsorption chromatography, e.g. column chromatography. Particularly preferred separation methods are those known as HPLC (High Performance Liquid Chromatography), SFC (Supercritical Fluid Chromatography), both in batch mode and in continuous mode, e.g. SMB (Simulated Moving Bed chromatography).

As is well known by the skilled person the term "stationary phase" relates to a suitable inert carrier material on which an interacting agent is immobilized. The term "reversed phase" relates to stationary phases in which alkyl chains are bonded to an inert carrier material. A suitable inert carrier material is preferably macroporous, e.g. silica gel, crosslinked polystyrene, polyacrylamide or zirconia. Silica gel is particularly preferred. Examples of "reversed phase" stationary phases are Symmetry C18 and Atlantis C18.

The term "mobile phase" relates to a solvent or mixture of solvents in which the mixture of compounds to be separated is dissolved. Suitable solvents to be used in the preparative chromatographic process according to the invention are the solvents that are known to be used in analytical chromatography. In "reversed phase" liquid chromatography as a rule polar, polar protic or aprotic solvents, or mixtures thereof are used. Suitable polar solvents are for example water in combination with methanol or acetonitrile. In supercritical chromatography, mixtures of carbon dioxide and polar protic solvents, e.g. methanol are preferred.

In an embodiment, columns used in preparative chromatography are vertical cylindrical tubes packed with chromatography media intended to bind the target molecules and then elute them slowly with a buffer and collecting various fractions of the eluent. The fractions containing the target molecule in its purest form are then pooled to obtain a desired degree of purification. However, the skilled person is aware that alternative configurations are available.

In a second aspect, the invention provides (1R,3S,5R,7R,8E,12R,14Z,16E,18E,20E,22R,24S,25R,26S)-22-[(3-amino-3,6-dideoxy-β-D-mannopyranosyl)oxy]-1,3,26-trihydroxy-12-methyl-10-oxo-6,11,28-trioxatricyclo[22.3.1.0$^{5,7}$]octacosa-8,14,16,18,20-pentaene-25-carboxylic acid of formula (II), $C_{33}H_{47}NO_{13}$, or a salt thereof.

(II)

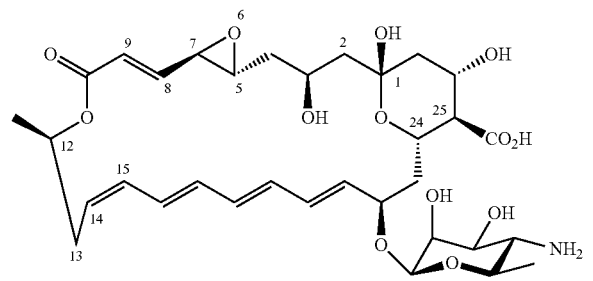

It was found that by performing the process of the first aspect of the invention the hitherto unknown compound of formula (II) can be isolated and subsequently analyzed and identified.

In an embodiment, the invention provides a composition comprising natamycin and the compound of formula (II) wherein the amount of said compound of formula (II) is from 0.001-0.1% (w/w) relative to the amount of natamycin. Preferably, the composition is isolated, for example by means of lyophilization, spray-drying or other means of removing a significant amount of water masses following the process for purifying natamycin of the first aspect of the invention. Consequently, the composition of the second aspect comprises from 0.001-10% (w/w) of water, or from 0.002-5% (w/w) of water, or from 0.005-3% (w/w) of water. In other words, the composition of the second aspect is a composition obtainable by a process for purifying natamycin comprising mixing a composition comprising crude natamycin, a metal salt of a carboxylic acid and water and subjecting the resulting mixture to chromatography whereby fractions are collected and selected fractions that comprise natamycin are combined, wherein the amount of said crude natamycin is from 1 g to 100 g/kg of the total weight of said composition and wherein the concentration of said metal salt of a carboxylic acid is from 0.1 mol/L to 5 mol/L. The composition can further provide another novel component, namely (1R,3S,5E,7R,11R,13E, 15E, 17E, 19E,21R,23S, 24R,25S)-21-[(3-amino-3,6-dideoxy-β-D-mannopyranosyl)oxy]-1,3,7,25-tetrahydroxy-11-methyl-9-oxo-10,27-dioxabicyclo[21.3.1]heptacosa-5, 13, 15, 17, 19-pentaene-24-carboxylic acid of formula (II), $C_{33}H_{49}NO_{13}$, or a salt thereof. The amount of the compound of formula (III) is from 0.001-0.1% (w/w) relative to the amount of natamycin.

(III)

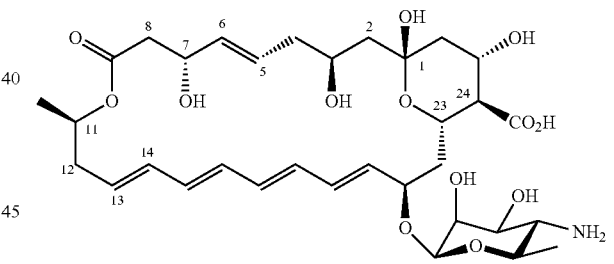

In a third aspect, the invention provides a process for preparing the compounds of the second aspect comprising subjecting natamycin or the mother liquor of re-crystallized natamycin to chromatography whereby fractions are collected and selected fractions that comprise said compounds are combined. Combined fractions may be concentrated to isolate the respective compounds. Concentration may be realized using tools available to the skilled person such as evaporation, lyophilization but also crystallization or precipitation followed by filtration.

An embodiment of the invention is the use of highly concentrated natamycin solutions that are subjected to chromatography. Thus, the chromatographic processes of the invention are advantageously carried out at unprecedented large scale. For example, when the chromatographic processes of the invention are carried out batch-wise, the amount of natamycin applied to the chromatographic material may be from 1 g to 10 kg per batch, or from 5 g to 5 kg per batch, or from 25 g to 1 kg per batch.

An embodiment of the invention is subjecting of the mother liquor of re-crystallized natamycin to preparative chromatography. Such a mother liquor may, for example, be obtained following re-crystallization of natamycin as described in WO 2006/045831. This can be dissolution of natamycin at high pH followed by crystallization at neutral pH or dissolution of natamycin at low pH followed by crystallization at neutral pH. The advantage of using the mother liquor of re-crystallized natamycin in preparative chromatography is in the fact that mother liquors are generally relatively higher in impurities compared to natamycin than the original crystals and certainly than the resulting crystals. Consequently, the use of the mother liquor of re-crystallized natamycin will lead to a higher yield of the desired compound following chromatography and/or a higher purity and/or a less elaborate procedure.

In a fourth aspect the invention provides the use of the compounds or the compositions of the second aspect in analysis of natamycin containing samples. Designing and optimizing natamycin production processes is best served when as many possible or probable side products or contaminants or the like are known. But importantly, not only known but also available to the technician enabling him to consistently repeat analytical procedures and obtain reliable results. The compounds and compositions of the instant invention are an addition to the toolbox of the skilled technician enabling him to further improve and optimize analytical procedures and consequently elevate not only process understanding but also product quality to a still higher level. These are constant needs in modern day product development.

In an embodiment, the compounds or the compositions of the second aspect may be used as standards and/or references in analytical methods such as High-Performance Liquid Chromatography, mass spectrometric analysis, Thin Layer Chromatography or NMR. Having access to larger quantities allows for constant availability and quality of the references and standards. Consequently, the compound of formula (II), but also that of formula (III), is industrially applicable for various purposes ranging from further optimization of natamycin production to potential antifungal activity in itself. The antifungal activity may be used in various food applications.

The invention is further described with reference to the following non-limiting examples.

EXAMPLES

General

HPLC in Combination with High Resolution Mass Spectrometer (LC-MS)
LC Column: Waters, Symmetry C18
  Mobile phase: Solvent A: 50 mM ammonium acetate buffer pH 5.8 Solvent B: Acetonitrile
  Injection volume: 10 µL
  Column temp.: 25° C.
  Flow rate: 1 mL/min
MS Instrument: LTQ Orbitrap
  LC/MS: Full scan ESI positive mode
  HPLC-UV Conditions for Fractionation

| Column: | Dr. Maische, NovoGROM Spherical C18, 100 Å, 250 × 4.6 mm, 15 µm |
|---|---|
| Mobile phase: | Solvent A: 50 mM ammonium acetate buffer pH 5.8 Solvent B: Acetonitrile |

| | Time (min.) | Solvent A (%) | Solvent B (%) |
|---|---|---|---|
| Gradient: | 0.0 | 75 | 25 |
| | 15.0 | 75 | 25 |
| | 21.0 | 65 | 35 |
| | 25.0 | 50 | 50 |
| | 26.0 | 75 | 25 |
| | 30.0 | 75 | 25 |

| | |
|---|---|
| Injection volume: | 100 µL |
| Column temp.: | 25° C. |
| Flow rate: | 1.0 mL/min. |
| Sample temp.: | 15° C. |
| Runtime (min.): | 30 minutes |
| Dionex Ultimate DAD-3000 (UV single wavelength) | |
| Wavelength | 305 nm |
| Bandwidth | 1 nm |
| Data collection rate | 5 Hz |
| Dionex Ultimate DAD-3000 (UV 3D) | |
| Wavelength2 | 200-600 nm |
| Bandwidth | 4 nm |
| Data collection rate | 5 Hz |
| Response time | 1 s |

The separation of compounds (I), (II), and (III) was verified using the conditions described above by means of high-resolution mass spectrometry. Start collecting 20 fractions of compounds (II), (III), and natamycin (I). Collected fractions were lyophilized for isolation of the respective compounds and further analyzed for structure elucidation.

For reference purposes NMR spectra of natamycin (I) were recorded on a Bruker Ascend 600 spectrometer. Methanol was used as chemical shift reference ($\delta$=31 ppm, 49.2 ppm). $^1$H and $^{13}$C chemical shifts were extracted from the $^1$H-$^{13}$C correlation (HSQC) spectrum.

Example 1

Preparation of (1R,3S,5R,7R,8E,12R,14Z,16E,18E,20E,22R,24S,25R,26S)-22-[(3-amino-3,6-dideoxy-β-D-mannopyranosyl)oxy]-1,3,26-trihydroxy-12-methyl-10-oxo-6,11,28-trioxatricyclo[22.3.1.0$^{5,7}$]octacosa-8,14,16,18,20-pentaene-25-carboxylic acid
(II)

Natamycin was produced by a culture of *Streptomyces natalensis* bacteria following a controlled fermentation process, for example as described in WO 97/29207 or references therein. A sample of the resulting broth was mixed with an aqueous potassium sorbate solution (3M) and the mixture was stirred until all natamycin was dissolved. The amount of aqueous potassium sorbate solution was such that the resulting concentration of natamycin was 10 g/L (w/w, 1%). In alternative, otherwise similar, experiments dissolution of natamycin was facilitated by raising the temperature to 40±10° C. for 30±20 min followed by cooling down to 20±2° C. The resulting solution was subjected to semi-preparative High-Performance Liquid Chromatography as described under General (HPLC-UV conditions for fractionation) above to isolate quantities of compound (II). In addition, fractions comprising a second compound of formula (III) were isolated. Samples were obtained as per the below Table. Contents of the samples were determined with LC-UV.

| Sample # | RT (min) | Natamycin I (mg/L) | II (mg/L) | III (mg/L) |
|---|---|---|---|---|
| 1 | 6.627 | n.a. | n.a. | n.a. |
| 2 | 8.363 | 0.02 | n.a. | 0.009 |
| 3 | 9.777 | 0.03 | n.a. | 0.007 |
| 4 | 11.173 | 0.03 | n.a. | 0.266 |
| 5 | 13.327 | 0.07 | n.a. | 0.018 |
| 6 | 14.333 | 0.32 | 0.581 | n.a. |
| 7 | 17.503 | 0.38 | n.a. | 0.034 |
| 8 | 20.140 | 134.93 | 0.714 | 0.307 |
| 9 | 23.377 | 403.18 | 1.694 | 0.465 |

The chemical structures were elucidated by Mass Spectrometry (MS) and Nuclear Magnetic Resonance (NMR).

Example 2

Structure elucidation of (1R,3S,5R,7R,8E,12R,14Z,16E,18E,20E,22R,24S,25R,26S)-22-[(3-amino-3,6-dideoxy-β-D-man nopyranosyl)oxy]-1,3,26-tri hydroxy-12-methyl-10-oxo-6,11,28-trioxatricyclo[22.3.1.0$^5$]octacosa-8,14,16,18,20-pentaene-25-carboxylic acid (II)

All material from the fraction comprising compound (II) obtained in Example 1 was adsorbed on a Sep-Pak column. The column was rinsed with $D_2O$ (1 mL). Next, the column was flushed with nitrogen gas. The column was eluted in the reversed direction with $CD_3CN$ (1 mL). Compound (II) did not elute from the column which was subsequently eluted with $CDCl_3/CD_3OD$ 1/1. The solution was transferred into an NMR tube, and further concentrated by means of a stream of nitrogen gas, until a volume of 0.65 mL was obtained. One drop of $D_2O$ was added to improve the linewidth in the NMR spectrum.

NMR spectra were recorded on a Bruker DRX 600 spectrometer, operating at a $^1H$ frequency of 600 MHz. An inverse probe equipped with gradient coils was used. In addition to a $^1H$ NMR spectrum, COSY, TOCSY and HSQC spectra were recorded. For chemical shift prediction ACD software version 4.04 was used.

TABLE

Chemical shifts of the characteristic carbons and protons in (II) and in natamycin (I) as compared to shifts predicted by ACD software version 4.04.

| Atom nr IUPAC | $^1H$ (ppm) | J (Hz) | $^{13}C$ (PPm) | ACD prediction $^1H$ | ACD prediction $^{13}C$ |
|---|---|---|---|---|---|
| Compound (II) | | | | cis | cis |
| 12 | 5.07 | | 71.0 | 4.93 | 67.8 |
| 13 | 2.62/2.39 | | 34.2 | 2.40 | 35.1 |
| 14 | 5.52 | ±9 (3x) | 127.6 | 5.60 | 127.6 |
| Natamycin (I) | | | | trans | trans |
| 12 | 4.69 | | 71.2 | 5.00 | 70.4 |
| 13 | 2.37/2.26 | | 40.6 | 2.34/2.30 | 41.5 |
| 14 | 5.57 | 5.7, 10.2, 14.6 | 128.7 | 5.62 | 129.7 |

Comparison of the 2D NMR spectra with those of natamycin (I) demonstrated that compound (II) differs from natamycin (I) only in the configuration of the double bond C14-C15, being cis in compound (II) and trans in natamycin (I). The pattern of coupling constants of H14 was in agreement with a cis-double bond on C14-C15. When the spectra of natamycin (I) and compound (II) were compared, it appeared that most signals had nearly identical chemical shifts, except those of C/H 12, 13 and 14. Moreover, the coupling pattern of H14 was very different from the pattern seen in natamycin (I). The slightly distorted quartet of H14 arose from three coupling constants of ±9 Hz, a typical value for a cis coupling, while a trans coupling usually has a magnitude of 12-18 Hz. Furthermore, the $^{13}C$ chemical shift of C13 has shifted 6 ppm upfield, being the expected upfield shift typical of a $CH_2$ adjacent to a cis double bond as compared to a trans double bond (ACD prediction). The chemical shifts of the relevant protons and carbons are listed in the above Table. From the results it was concluded that compound (II) is an isomer of natamycin (I) with a cis double bond between C14 and C15.

Example 3

Structure Elucidation of (1R,3S,5E,7R,11R,13E,15E,17E,19E,21R,23S,24R,25S)-21-[(3-amino-3,6-dideoxy-β-D-mannopyranosyl)oxy]-1,3,7,25-tetra-hydroxy-11-methyl-9-oxo-10,27-dioxabicyclo[21.3.1]heptacosa-5,13,15,17,19-pentaene-24-carboxylic acid (III)

All material from the fraction comprising compound (III) obtained in Example 1 were dissolved in $CD_3OD$ (0.6 mL). The sample presumably contained a large amount of glycerol, introduced as a contaminant during freeze-drying. Also signals of free fatty acids were dominant. NMR spectra were recorded on a Bruker Ascend 700 spectrometer operating at a proton frequency of 700 MHz equipped with a TCI cryo probe and measured with a probe temperature of 300K with suppression of the water signal. A 1D $^1H$ spectrum was obtained with 256 scans in 30 minutes, a COSY spectrum was recorded with 8 scans and 800 increments in F1 in 3 hours, TOCSY spectra were recorded with 8 scans and mixing times of 40 and 100 ms and 800 increments in the F1 dimension in 3 hours each. A $^1H$-$^{13}C$ correlation (HSQC) spectrum was recorded with 288 scans and 512 increments in the F1 dimension in 55 hours.

From the $^1H$ NMR spectrum it was clear that the signal of H9 of natamycin was missing. Identification of the compound in this fraction was possible by comparing the proton carbon correlation spectrum (HSQC) and the proton-proton correlation spectrum (COSY) with those of natamycin. Overlaying the HSQC spectrum of natamycin and that of this fraction showed that most signals had (near) identical chemical shifts with the exception of those at atom numbers 5,6,7,8 and 11 of the compound of formula (II) (note that atoms 5, 6, 7, 8 and 11 in (III) are 5, 7, 8, 9 and 12 respectively in (I)). With the aid of the COSY spectrum and the molecular formula given by LC/MS (natamycin+2H) the abovementioned signals were assigned, and it was concluded that the impurity has the structure as given in formula (III).

The characteristic doublet of natamycin (I) of H9 at 6.06 ppm has disappeared, and instead H8 in (III) appeared as two mutually coupled signals at 2.28 and 2.50 ppm. These chemical shifts strongly indicate a $CH_2$ group. Furthermore, the characteristic double doublet of H8 in natamycin (I) has disappeared, and the proton signal of H7 in (III) was identified at 4.29 ppm, which is strongly indicative of a CH(OH) group. Finally, H7 and H5 in (I) were found at 3.14 and 2.82 ppm, respectively, in agreement with the epoxide moiety. In the analysis, these proton signals, labelled H6 and H5 were both found at 5.48 ppm. Chemical shifts of the protons and carbons that differ significantly from those in natamycin are given in the below Table. These $^1H$ and $^{13}C$ chemical shifts were extracted from the $^1$H-$^{13}$C correlation (HSQC) spectrum. The multiplicity of the $^1$H signals was not given, as all the proton signals partially overlap with other signals.

TABLE

Chemical shifts of the characteristic carbons and protons in (III) as compared to shifts predicted by ACD software version 4.04.

| Atom nr (IUPAC) | $^1$H (ppm) | $^{13}$C (ppm) | ACD prediction $^1$H trans | ACD prediction $^{13}$C trans | ACD prediction $^1$H cis | ACD prediction $^{13}$C cis |
|---|---|---|---|---|---|---|
| 8 | 2.50/ 2.28 | 44.5 | 2.5 | 42 | 2.5 | 42 |
| 7 | 4.29 | 70.4 | 4.6 | 67 | 4.4 | 63 |
| 6 | 5.45 | 130.5 | 5.7 | 132 | 5.7 | 127 |
| 5 | 5.45 | 135.7 | 5.7 | 114 | 5.7 | 127 |
| 11 | 4.92 | 71.5 | 4.6 | 74 | 4.6 | 74 |

The invention claimed is:

1. A process for purifying natamycin comprising mixing a composition comprising crude natamycin, a metal salt of a carboxylic acid and water and subjecting the resulting mixture to chromatography whereby fractions are collected and selected fractions that comprise natamycin are combined, wherein the amount of said crude natamycin is from 1 g to 100 g/kg of the total weight of said composition and wherein the concentration of said metal salt of a carboxylic acid is from 0.1 mol/L to 5 mol/L.

2. The process according to claim 1 wherein said mixing is carried out at a temperature of from 30° C. to 130° C. wherein said temperature is maintained for from 10 to 200 minutes.

3. The process according to claim 1, wherein said metal is an alkali metal or an alkali earth metal.

4. The process according to claim 1, wherein said carboxylic acid is acetic acid, benzoic acid, citric acid, formic acid, lactic acid, propionic acid, sorbic acid or a mixture thereof.

5. The process according to claim 4, wherein said carboxylic acid is sorbic acid.

6. A composition comprising natamycin and a compound of formula (III) (1R,3S,5E,7R,11R, 13E, 15E,17E, 19E,21R, 23S,24R,25S)-21-[(3-Amino-3,6-dideoxy-β-d-man nopyranosyl) oxy]-1,3,7,25- tetrahydroxy-11-methyl-9-oxo-10,27-dioxabicyclo [21.3.1] hepta cosa-5,13, 15, 17,19-pentaene-24-carboxylic acid or a salt thereof, wherein the amount of said compound of formula (III) or salt thereof is from 0.001-0.1% (w/w) relative to the amount of natamycin

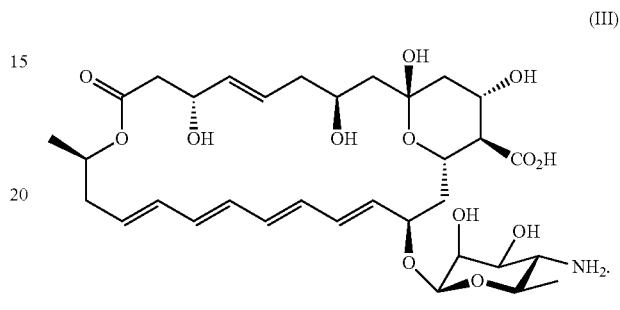

(III)

7. A process for preparing the composition according to claim 6 comprising subjecting natamycin or a mother liquor of re-crystallized natamycin to chromatography whereby one or more fractions are collected and selected fractions that comprise said compound or salt thereof are combined.

8. The process according to claim 7, wherein said combined selected fractions are concentrated.

9. The process according to claim 8 wherein the fractions are concentrated by lyophilization.

10. The process according to claim 7 wherein the chromatography is carried out with from 1 g to 10 kg of natamycin per batch.

* * * * *